United States Patent [19]

Pert et al.

[11] 4,371,463

[45] Feb. 1, 1983

[54] ENZYME-RESISTANT OPIATE PENTAPEPTIDES

[75] Inventors: Candace B. Pert, Bethesda, Md.; Jaw-Kang Chang, Pulerton, Calif.

[73] Assignee: The United States of America as represented by the Department of Health and Human Services, Washington, D.C.

[21] Appl. No.: 769,686

[22] Filed: Feb. 17, 1977
(Under 37 CFR 1.47)

[51] Int. Cl.³ .................... C07C 103/52; A61K 37/00
[52] U.S. Cl. ................. 260/112.5 E; 424/177
[58] Field of Search ................. 424/177; 260/112.5 E

[56] References Cited

U.S. PATENT DOCUMENTS

| | | | |
|---|---|---|---|
| 4,028,319 | 6/1977 | Jones, Jr. et al. | 424/177 |
| 4,038,222 | 7/1977 | Li | 424/177 |
| 4,254,106 | 3/1981 | Wilkinson | 260/112.5 E |

OTHER PUBLICATIONS

L. Terenius et al., Biochem. and Biophys. Res. Commun. 71, 1976, pp. 175–179.
C. Pert et al., Science 194, 1976, pp. 330–332.
D. H. Coy et al., Biochem. and Biophys. Res. Commun. 73, 1976, pp. 632–638.
H. E. Bleich et al., Biochem. and Biophys. Res. Commun. 74, 1977, pp. 592–598.

*Primary Examiner*—Delbert R. Phillips
*Attorney, Agent, or Firm*—Holman & Stern

[57] ABSTRACT

Pentapeptides having the formula
H-L-Tyr-A-Gly-L-Phe-B-R wherein A is a D-amino acid residue, Sar or L-Pro, B is L-Met of L-Leu, and R is $NH_2$ or OH. These pentapeptides are synthetic analogues of the naturally-occurring Met-and Leu-enkephalins and possess opiate activity which is resistant to destruction by body enzymes.

3 Claims, No Drawings

ENZYME-RESISTANT OPIATE PENTAPEPTIDES

BACKGROUND OF THE INVENTION

This invention relates to novel pentapeptides and, more particularly, to synthetic analogues of the naturally-occurring pentapeptides, Met-enkephalin and Leu-enkephalin.

It has recently been established that morphine and other opiates initiate their pharmacological effects by complexing reversibly with opiate receptors, which are stereo-specific components of vertebrate synaptic membranes distributed heterogeneously in the mammalian nervous system. A number of endogenous peptides which appear to serve as natural ligands for these opiate receptors, have been demonstrated to exist in brain, pituitary, human cerebrospinal fluid and human blood. The first of these natural ligands to be identified was extracted from porcine brain by Hughes et al. (Nature, Volume 258, Page 577, 1975) and termed "enkephalin," which was found to be a mixture of two pentapeptides having the formulas H-L-Tyr-Gly-Gly-L-Phe-L-Met-OH (Met-enkephalin) and H-L-Tyr-Gly-Gly-L-Phe-L-Leu-OH (Leu-enkephalin).

Both enkephalins when tested in vitro have been found to have a high affinity for opiate receptors, which is generally predictive of opiate potency in vivo. However, extremely high quantities of enkephalin (120–200 µg) are required to elicit analgesia when microinjected into rat cerebral ventricles and brain. Thus, Met-enkephalin is at least 50-fold weaker than morphine as an analgesic despite the fact that it possesses about half of the affinity of morphine for rat brain opiate receptors. Moreover, Met-enkephalin's mild analgesia dissipates completely in several minutes, even when injected directly into active brain sites where morphine induces analgesia which persists for several hours. This apparent discrepancy between in vivo and in vitro potency is explained by the finding that enkephalin's affinity for opiate receptors is rapidly and efficiently destroyed by the action of body enzymes which cause degradation of the peptide bonds. Hence, due to its only very transient pharmacological effects, enkephalin has little, if any, potential therapeutic value.

SUMMARY OF THE INVENTION

It is, accordingly, a primary object of the present invention to provide novel peptides possessing therapeutically effective opiate activity.

Another object of the invention is to provide synthetic analogues of the enkephalins which are resistant to degradation by body enzymes.

A further object of the invention is to provide enzyme-resistant synthetic enkephalin analogues which retain high affinity for opiate receptors.

Still another object of the invention is to provide enzyme-resistant synthetic enkephalin analogues which possess relatively long-acting therapeutically effective opiate activity.

The above and other objects are achieved in accordance with the present invention by providing novel pentapeptides selected from the group consisting of H-L-Tyr-A-Gly-L-Phe-B-R (I)

and their pharmaceutically acceptable non-toxic acid addition salts, wherein A is an amino acid residue having a structure capable of protecting its peptide bond with the terminal L-Tyr against enzymatic cleavage, B is L-Met or L-Leu, and R is $NH_2$ or OH. More specifically, A is preferably a D-amino acid residue, but alternatively may be Sar or L-Pro.

The above-defined pentapeptides in accordance with the present invention have a high affinity for opiate receptors, are resistant to enzymatic degradation, and exhibit relatively long-lasting potent therapeutically effective opiate activity which is not destroyed by the action of body enzymes.

DESCRIPTION OF PREFERRED EMBODIMENTS

The pentapeptides encompassed by Formula I above, are analogues of Met-enkephalin, Leu-enkephalin or their carboxyl terminal amides, wherein the glycyl (Gly) at the 2-position has been replaced with an amino acid residue having a structure capable of protecting its peptide bond with the terminal tyrosyl (Tyr) against enzymatic cleavage. All of the standard D-amino acid residues, as well as sarcosyl (Sar) and L-prolyl (L-Pro), have structures meeting this requirement. It has been found that the peptide bond between the terminal Tyr and the Gly in the 2-position of the enkephalins is particularly susceptible to enzymatic cleavage, and that protection of this peptide bond against enzymatic cleavage by means of the above-described substitution at the 2-position conveys to the resulting pentapeptide resistance to degradation by body enzymes.

While degradative enzyme resistance is conveyed to the pentapeptides of Formula I by means of any of the standard D-amino acid residues at the 2-position thereof, D-alanyl (D-Ala), D-phenylalanyl (D-Phe) and D-valyl (D-Val) have been found to be particularly suitable for this purpose. Other D-amino acid residues which can be used in place thereof as A in Formula I include, for example, D-leucy (D-Leu), D-isoleucyl (D-Lle), D-prolyl (D-Pro), D-methionyl (D-Met), D-seryl (D-ser), D-threonyl (D-Thr), D-asparagyl (D-Asn), D-cysteinyl (D-Cys), D-tyrosyl (D-Tyr), D-glutaminyl (D-Gln), D-tryptophyl (D-Try), D-aspartyl (D-Asp), D-histidyl (D-His), D-glutamyl (D-Glu), D-lysyl (D-Lys) and D-arginyl (D-Arg). In contrast, it should be noted that the degradative enzyme-resistant properties possessed by the pentapeptides of the present invention are not obtained when the 2-position thereof is occupied by any of the corresponding L-amino acid residues other than L-Pro.

Illustrative of pharmaceutically acceptable non-toxic addition salts of the pentapeptides of Formula I are hydrochloride, hydrobromide, sulfate, phosphate, maleate, acetate, citrate, benzoate, succinate, malate, ascorbate, and the like.

The pentapeptides of Formula I may be readily prepared by routine solid phase peptide synthesis techniques well known in the art and described, for example, by Stewart and Young, "Solid Phase Peptide Synthesis" (W. H. Freeman and Co., San Francisco, 1969). The synthesis is commenced from the carboxyl terminal end of the peptide by coupling the appropriate amino acid, i.e., either L-methionine or L-leucine, to a suitable resin support, such as a benzhydrylamine resin, a chloromethylated resin or a hydroxymethyl resin. The coupling reaction is carried out with the aid of a carboxyl group-activating compound such as dicyclohexylcarbodiimide, and with the α-amino group of the amino acid protected with a protecting group, such as t-butyloxycarbonyl. Following this coupling reaction, the α-amino protecting group is removed, such as by using trifluoroacetic acid in methylene chloride, trifluoroacetic acid alone or HCl in dioxane, with the deprotection being carried out at a temperature between about 0° C. and room temperature. Thereafter, each succeeding amino acid in the sequence is coupled in the same manner step-wise in the desired order to obtain the pentapeptide of Formula I. As an alternate to adding each amino acid separately to the reaction, some of them may be coupled prior to addition to the solid phase reactor. Each protected amino acid or amino acid sequence is introduced into the solid phase reactor in about a fourfold excess and the coupling is carried in a medium of dimethylformamide: methylene chloride (1:1) or in dimethylformamide or methylene chloride alone. The success of the coupling reaction at each stage of the synthesis is monitored by the ninhydrin reaction as described by E. Kaiser et al., Analyt. Biochem., 34, 595 (1970).

After the final α-amino protected amino acid in the sequence, i.e., L-tyrosine, has been coupled, the deprotection step is carried out by treatment with a reagent such as hydrogen fluoride which not only cleaves the α-amino protecting group from the tyrosine and any remaining side chain protecting groups from the peptide, but also cleaves the peptide from the resin support. When a benzhydrylamine resin has been used as the resin support, the peptide thereby cleaved from the resin will be in the carboxyl terminal amide form of the peptide of Formula I. When a chloromethylated resin or a hydroxymethyl resin has been used as the resin support, the peptide cleaved from the resin support will be in the form of the carboxyl terminal benzyl ester, which may then be readily converted by methods well known in the art to the free acid or carboxyl terminal amide forms of the peptide of Formula I.

The pentapeptides in accordance with the present invention have been found to possess a high affinity for opiate receptors which, due to the degradative enzyme-resistant properties of these pentapeptides, is not susceptible to rapid destruction by the action of body enzymes. This combination of opiate receptor affinity coupled with degradative enzyme resistance, the latter not being possessed by the naturally-occurring enkephalins, renders the synthetic enkephalin analogues of the present invention therapeutically valuable as long-lasting opiate drugs.

The pentapeptides encompassed by Formula I have varying degrees of opiate receptor affinity, and hence varying degrees of potency as opiate drugs, depending upon the particular amino acid residues employed in the 2-position (A in the formula) and in the 5-position (B in the formula), and, in some cases, upon the carboxyl terminal group employed (R in the formula). In general, the Met-enkephalin analogue (B is L-Met) will have a somewhat higher opiate receptor affinity than the corresponding Leu-enkephalin analogue (B is L-Leu), and the carboxyl terminal amide (R is $NH_2$) will have a slightly higher opiate receptor affinity than the corresponding free acid (R is OH). The most critical variation in Formula I affecting opiate receptor affinity is A, with the highest opiate receptor affinity being exhibited when A is D-Ala.

The preferred pentapeptides in accordance with the present invention are those having the formula H-L-Tyr-D-Ala-Gly-L-Phe-L-Met-R     (II)

wherein R is $NH_2$ or OH. The enkephalin analogues of Formula II have been termed D-Ala$^2$-Met-enkephalin-amide (R is $NH_2$) and D-Ala$^2$-Met-enkephalin (R is OH), respectively. Both of these enkephalin analogues have been found to exhibit an equally high level of opiate receptor affinity which is greater than that exhibited by the naturally-occurring Leu-enkephalin and almost as great as that exhibited by the naturally-occurring Met-enkephalin.

The therapeutic effectiveness of the pentapeptides in accordance with the present invention as opiate drugs has been demonstrated by tests carried out on rats. When microinjected into rat brain, the pentapeptides of the present invention were found to elicit profound, long-lasting, morphine-like analgesia, at relatively low dose levels varying with the particular enkephalin analogue employed. For example, both D-Ala$^2$-Met-enkephalin-amide and D-Ala$^2$-Met-enkephalin at dose levels of 5–10 μg were found to elicit analgesic effects almost as potent and long-lasting as that elicited by comparable dose levels of morphine, with a duration of action of several hours. Such analgesic effects were not observed, however, when the pentapeptides were administered by intravenous injection, indicating that these pentapeptides do not cross the blood-brain barrier. Since some important therapeutic effects of opiates are on smooth muscle directly and are medicated by peripheral opiate receptors rather than by the brain, the pentapeptides of the present invention are therapeutically valuable in situations where mental opiate effects, such as euphoria and analgesia, are undesirable, and peripheral opiate effects, such as gastrointestinal suppression, are needed. In such applications, the pentapeptides could be administered intravenously, intramuscularly or orally, with the effective dosage varying with the form of administration, the particular host animal, and the particular pentapeptide analogue employed. For example, when using D-Ala$^2$-Met-enkephalin-amide or D-Ala$^2$-Met-enkephalin as an anti-diarrheal agent in humans, dose levels of approximately 5–20 mg per person would be appropriate for intravenous or intramuscular administration, while dose levels of 20–100 mg per person would be appropriate for oral administration.

The invention is further illustrated by way of the following examples.

EXAMPLE 1

Synthesis of D-Ala$^2$-Met-enkephalin-amide

Benzhydrylamine resin (20.0 g) is put in a Merrifield vessel of 300 ml capacity and put through the following wash cycle: (a) methylene chloride; (b) trifluoroacetic acid (three times for ten minutes each); (c) methylene chloride; (d) methanol; (e) triethylamine 12.5% in dimethylformamide (two times for ten minutes each); (f) methanol (two times); (g) methylene chloride (two times), allowing a contact time of at least three minutes each, if not indicated otherwise.

The resin so prepared is then gently shaken with t-butyloxycarbonyl (t-Boc) L-methionine (21 mmole), in 1:1 methylene chloride-dimethylformamide and 25.6 ml of 1 M dicyclohexylcarbodiimide in methylene chloride is added in three portions over a period of thirty minutes. Shaking is continued at ambient temperature for a total of 18 hours. The peptide-resin is then washed successively with methanol, methylene chloride, methanol (twice), and methylene chloride (twice). To test for completeness of reaction, the peptide-resin is subjected to a ninhydrin test following the procedure of E. Kaiser et al., Analytical Biochemistry, 34, 595 (1970).

The attached amino acid residue is then deprotected by treating the peptide-resin with a 1:1 solution of trifluoroacetic acid-methylene chloride (three times for fifteen minutes each). Then steps (c) through (g), as described above for the wash cycle, are performed.

The peptide-resin is then subjected to successive repetitions of the above-described coupling procedure, substituting for the t-Boc-L-methionine the following α-amino protected amino acids in the following order: t-Boc-L-phenyl-alanine, t-Boc-glycine, t-Boc-D-alanine, and t-Boc-L-tyrosine. Removal of the α-amino protecting group following each but the final coupling step is performed as described above for the deprotection of the t-Boc-L-Met-resin. After coupling of the t-Boc-L-tyrosine, the washed peptide-resin is dried in vacuo. Removal of the protecting groups and cleavage of the pentapeptide from the resin is then accomplished by treating the dried peptide-resin in vacuo with liquid hydrogen fluoride (25 ml) and anisole (10 ml) at ice bath temperature for one hour. The hydrogen fluoride is removed by vacuum distillation and the anisole removed by washing with ether. The pentapeptide is dissolved in 10% acetic acid, removed from the resin by filtration, and lyophilized.

Thin layer chromatography of the resulting D-Ala$^2$-Met-enkephalin-amide in three solvent systems (1=CHCl$_3$:MeOH:NH$_4$OH, 60:30:5, silica gel; 2=n-BuOH:HOAc:H$_2$O, 4:1:5 upper layer, cellulose; 3=n-BuOH:pyridine:HOAc:H$_2$O 15:10:3:12, silica gel) and high voltage electrophoresis (4,000 V, one hour, pH 5.6 pyridine acetate buffer, Whatman No. 1 paper, in which the pentapeptide moved toward the cathode using Met-enkephalin as the internal standard) yields the following analysis: $R_f{}^1=0.85$, $R_f{}^2=0.82$, $R_f{}^3=0.77$; electrophoresis=2.64. Amino acid analysis gives the following ratios: Met 1.00, Gly 1.03, Ala 0.95, Tyr 0.98, Phe 1.04, NH$_3$ 0.98.

In like manner, the other pentapeptides of Formula I may be readily synthesized by replacing either or both of the t-Boc-L-methionine and the t-Boc-D-alanine with the appropriate α-amino protected amino acid. The free acid form of pentapeptide may be readily obtained, for example, by using a chloromethylated resin as the resin support in place of the benzhydrylamine resin, cleaving the pentapeptide from the resin support by methanolysis and converting the resulting carboxyl terminal methyl ester to the free acid by hydrolysis.

EXAMPLE 2

The pentapeptides of the present invention were assessed for opiate receptor affinity by the inhibition of stereospecific $^3$H-naloxone binding to rat brain membranes, under conditions which have previously been found to avoid the enzymatic destruction of the naturally-occurring peptides which normally occurs at physiological conditions. Male rats weighing 180–200 g (Sprague-Dawley) were decapitated and each brain with the cerebellum removed was homogenized in 150 mls of ice-cold standard buffer (0.05 M Tris-HCl, pH 7.0 at 25° C.). After refrigerated centrifugation at 12,000×g, the membranes were reconstituted in the standard buffer. After recentrifugation, each brain was suspended in 10 mls of the standard buffer. Aliquots of the freshly prepared membrane preparation (100 μl) were incubated for one hour at 0° C. with various concentrations of the pentapeptide and 100 mM NaCl in a final volume of 0.5 ml with $^3$H-naloxane (New England Nuclear, 34 Ci/mmole) in a concentration of 1.3 nM (20,000 cpm). Incubation was begun with the addition of brain membranes, which were added last. After rapid filtration and washing with two 7 ml portions of ice-cold standard buffer, membrane-laden filters were transferred and counted at 40–45% efficiency at least six hours after shaking with detergent scintillation fluor (Aquasol, New England Nuclear). Control incubations containing levallorphan (100 nM) or dextrallorphan (100 nM) were included. Stereospecific binding ($^3$H-naloxone bound in the presence of levallorphan subtracted from binding in the presence of dextrallorphan) represented 85–90% of the total bound naloxane in all experiments. Control values in all experiments ranged between 2000–2800 cpm. From a plot of the percent inhibition of stereospecific $^3$H-naloxane binding as a function of pentapeptide concentration, the opiate receptor affinity of the pentapeptide was determined as that concentration of pentapeptide, in μM, causing 50% inhibition of stereospecific $^3$H-naloxone binding. In this test, the lower the numerical value obtained, the higher is the opiate receptor affinity of the pentapeptide.

Table I below lists the opiate receptor affinities obtained with six of the pentapeptides in accordance with the present invention, namely, D-Ala$^2$-Met-enkephalin, D-Ala$^2$-Met-enkephalin-amide, D-Phe$^2$-Met-enkaphalin-amide (the pentapeptide of Formula I wherein A is D-Phe, B is L-Met, and R is NH$_2$), D-Val$^2$-Met-enkephalin-amide (the pentapeptide of Formula I wherein A is D-Val, B is L-Met, and R is NH$_2$), Sar$^2$-Met-enkephalin-amide (the pentapeptide of Formula I wherein A is Sar, B is L-Met, and R is NH$_2$), and L-Pro$^2$-Met-enkephalin-amide (the pentapeptide of Formula I wherein A is L-Pro, B is L-Met, and R is NH$_2$). For purposes of comparison, Table I also includes the opiate receptor affinity values obtained for the naturally-occurring Met-enkephalin and Leu-enkephalin, as well as for L-Ala$^2$-Met-enkephalin-amide (the isomer of D-Ala$^2$-Met-enkephalin-amide wherein the D-Ala in the 2-position is replaced with the "natural" enantiomer, L-Ala).

TABLE 1

| Pentapeptide | Opiate Receptor Affinity |
|---|---|
| D-Ala$^2$-Met-enkephalin | 0.4 |
| D-Ala$^2$-Met-enkephalin-amide | 0.4 |
| D-Phe$^2$-Met-enkephalin-amide | 2.0 |
| D-Val$^2$-Met-enkephalin-amide | 4.0 |
| Sar$^2$-Met-enkephalin-amide | 8.0 |
| L-Pro$^2$-Met-enkephalin-amide | 90 |
| Met-enkephalin | 0.2 |
| Leu-enkephalin | 0.7 |
| L-Ala$^2$-Met-enkephalin-amide | 4.0 |

As can be seen from Table I, the pentapeptides in accordance with the present invention all have relatively high levels of opiate receptor affinity of varying degree. The two most active pentapeptides of the present invention, D-Ala$^2$-Met-enkephalin and D-Ala$^2$-Met-enkephalin-amide, exhibit equally high opiate receptor affinities which are almost as great as the naturally-occurring Met-enkephalin, slightly greater than that exhibited by the naturally-occurring Leu-enkaphalin, and 10-fold greater than that exhibited by the corresponding L-Ala$^2$ isomer.

EXAMPLE 3

Each of the pentapeptides listed in Table 1 above, at concentrations chosen to produce approximately 80% inhibition of stereospecific $^3$H-naloxone binding, were preincubated for various times up to 60 minutes with well-washed rat brain membranes under physiological conditions at 37° C. The preincubations were terminated by brief (1-2 minutes) immersion of the test tubes into boiling water and centrifugation at 12,000×g for 5 minutes which produced a clear supernatant fluid, which was then assessed for opiate receptor inhibitory activity as described above in Example 2.

Complete loss of opiate receptor inhibitory activity resulted after 20 minutes of the preincubation with both of the naturally-occurring Met-enkephalin and Leu-enkephalin, and after 60 minutes of the preincubation with the L-Ala$^2$-Met-enkephalin-amide. In contrast, no significant loss of opiate receptor inhibitory activity resulted after 60 minutes of the preincubation with each of the pentapeptides in accordance with the present invention. These test results indicate the degradative enzyme-resistant properties of the pentapeptides of the present invention under physiological conditions which cause complete inactivation of the opiate receptor affinity of the naturally-occurring enkephalins as well as of the L-Ala$^2$ analogue.

EXAMPLE 4

The opiate activity in vivo of the pentapeptides of the present invention was demonstrated by tests carried out on rats employing intracerebral injection techniques. Sprague-Dawley rats were stereotaxically implanted with chronic indwelling cannulae guides constructed from 23 gauge TW stainless steel tubing and fitted with stilettes of corresponding length. The guide cannulae tips were aimed for an area 2 mm dorsal to the periaqueductal gray matter of the mesencephalon, which has been found to mediate the analgesic actions of opiates in rodents and primates. Testing was initiated approximately one week following surgery. The compounds being assessed for analgesic activity were dissolved in pyrogen-free water and microinjected at various dose levels in a volume 1 μl through 30 gauge injectors which protruded 2 mm past the guide cannulae tips.

Analgesia was assessed by the D'Amour and Smith "tail-flick" procedure, the "flinch-jump" test, and by subjectively evaluating an animal's reaction to pinches of the limbs with forceps. In the "tail-flick" test, a high intensity light was focused on a rat's tail which had been blackened with a felt-tip pen, and the time that it took an animal to remove its tail from this radiant heat was measured to the nearest 0.5 second. In the "flinch-jump" test, AC shock intensity at which an animal jumped and squealed was quantified 15 minutes after an injection (immediately after testing in the tail-flick test). Reactions to limb pinches were also noted at this time. Baseline measures were always taken approximately one hour prior to injection. All animals were tested at 1, 5, 15, 30, 60, 120, and 180 minutes after injection and then at one hour intervals until their response latencies had recovered to baseline levels.

The results of these tests indicated that D-Ala$^2$-Met-enkephalin-amide at dose levels of 5-10 μg was quite effective in eliciting analgesia which persisted for as long as three hours after injection. By way of comparison, the analgesia induced by 10 μg of this pentapeptide persisted for about the same length of time as that induced by 5 μg of morphine, but was not as intense at 1 and 2 hours after injection. Rats which received a preinjection of the opiate antagonist naloxone (2 mg/kg, i.p.) 15 minutes before microinjection of 10 μg of D-Ala$^2$-Met-enkephalin-amide showed almost complete reversal of analgesia. The results obtained with D-Ala$^2$-Met-enkephalin were quite similar to those obtained with D-Ala$^2$-Met-enkephalin-amide, while a dose level of 20 μg of D-Val$^2$-Met-enkephalin-amide was needed to produce the same analgesic response as that produced by 5 μg of D-Ala$^2$-Met-enkephalin-amide. By way of comparison, 10 μg of L-Ala$^2$-Met-enkephalin-amide failed to elicit any significant analgesia, while the relatively low level of analgesia elicited by 120 μg of the naturally-occurring Met-enkephalin rapidly declined and returned to pre-drug level by 5 minutes after injection.

The embodiments of the invention in which an exclusive property or privilege is claimed are defined as follows:

1. A compound of the formula

H-Tyr-Sar-Gly-Phe-Y-R wherein Y is Leu or Met; R is OH or NH$_2$; and the stereochemical configuration of each of the optically active amino acid residues is L.

2. The compound according to claim 1 which is L-tyrosylsarcosylglycyl-L-phenylalanyl-L-methionine or its carboxyl terminal amide.

3. The compound according to claim 1 which is L-tyrosylsarcosylglycyl-L-phenylalanyl-L-leucine or its carboxyl terminal amide.

* * * * *